US010857009B2

(12) United States Patent
Hugate, Jr.

(10) Patent No.: US 10,857,009 B2
(45) Date of Patent: Dec. 8, 2020

(54) HYBRID COMPRESS BONE FIXATOR (71) Applicant: Zimmer, Inc., Warsaw, IN (US)

(72) Inventor: Ronald Raymond Hugate, Jr., Highlands Ranch, CO (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 16/017,184

(22) Filed: Jun. 25, 2018

(65) Prior Publication Data
US 2018/0368995 A1 Dec. 27, 2018

Related U.S. Application Data (60) Provisional application No. 62/604,152, filed on Jun. 26, 2017.

(51) Int. Cl.
*A61F 2/78* (2006.01)
*A61F 2/28* (2006.01)
*A61B 17/72* (2006.01)
*A61F 2/30* (2006.01)

(52) U.S. Cl.
CPC ............ *A61F 2/78* (2013.01); *A61B 17/7225* (2013.01); *A61F 2/2814* (2013.01); *A61F 2/30749* (2013.01); *A61F 2002/7806* (2013.01); *A61F 2002/7887* (2013.01)

(58) Field of Classification Search
CPC ............... A61F 2/2814; A61F 2/30749; A61F 2002/7887
USPC ..................................................... 606/62–64
See application file for complete search history.

(56) References Cited

U.S. PATENT DOCUMENTS

| 5,282,861 | A | 2/1994 | Kaplan |
| 6,015,437 | A * | 1/2000 | Stossel ....................... A61F 2/40 623/19.11 |
| 7,141,073 | B2 * | 11/2006 | May ...................... A61B 17/164 623/32 |
| 7,468,078 | B2 * | 12/2008 | Sederholm .......... A61F 2/30734 623/22.42 |
| 7,892,290 | B2 * | 2/2011 | Bergin .................. A61F 2/3662 623/23.46 |
| 8,771,271 | B2 * | 7/2014 | Overes ............... A61B 17/1725 606/62 |
| 8,915,970 | B2 * | 12/2014 | Porter ....................... A61F 2/78 623/16.11 |
| 9,078,714 | B2 * | 7/2015 | Allinniemi ......... A61B 17/0401 |

(Continued)

FOREIGN PATENT DOCUMENTS

DE          808974          7/1951

OTHER PUBLICATIONS

"European Application Serial No. 18179960.2, Extended European Search Report dated Nov. 28, 2018", 6 pgs.

*Primary Examiner* — Marcia L Watkins
(74) *Attorney, Agent, or Firm* — Schwegman Lundberg & Woessner, P.A.

(57) ABSTRACT

A stem for fixating a prosthesis to a bone can include a first stem portion and a second stem portion. The first stem portion can extend substantially along a longitudinal axis. The first stem portion can include a distal portion. The second stem portion can extend substantially distally from the distal portion of the first stem portion along the longitudinal axis. The second stem portion can be securable to the bone, and the second stem portion can include a distal portion couplable to a compress assembly.

13 Claims, 3 Drawing Sheets

(56) References Cited

U.S. PATENT DOCUMENTS

| | | | |
|---|---|---|---|
| 2001/0020187 A1* | 9/2001 | Guettinger | A61F 2/30724 623/23.25 |
| 2002/0099449 A1* | 7/2002 | Speitling | A61F 2/30767 623/23.72 |
| 2008/0009951 A1* | 1/2008 | Hodge | A61B 17/1753 623/20.35 |
| 2014/0214177 A1 | 7/2014 | Porter et al. | |
| 2014/0228973 A1 | 8/2014 | Porter | |
| 2015/0073489 A1* | 3/2015 | Finley | A61B 17/844 606/320 |
| 2015/0305897 A1 | 10/2015 | Hershberger et al. | |

* cited by examiner

HYBRID COMPRESS BONE FIXATOR

CLAIM OF PRIORITY

This application claims the benefit of U.S. Provisional Patent Application Ser. No. 62/604,152, filed on Jun. 26, 2017, the benefit of priority of which is claimed hereby, and which is incorporated by reference herein in its entirety.

BACKGROUND

The present subject matter relates to orthopedic prostheses and, more particularly, to prostheses, systems, and methods used with prosthetic limbs. Orthopedic procedures and prostheses are commonly utilized to repair and/or replace damaged bone and tissue in the human body. For example, an above-the-knee amputation can also include installation of an implant anchored to a femur of a patient. A compress implant creates compression at a bone-to-implant interface causing subsequent reactive bone stimulation and formation that results in osseous integration.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

In some circumstances, a patient may require a bone implant to adapt a resected bone for connection to an external prosthesis. One type of implant is a compress where compression to the bone/implant interface can be achieved through the placement of an anchoring plug or stem within the intramedullary canal of the bone. In some examples, a series of transversely oriented pins are placed through the bone and through pre-drilled holes in the stem to act as a base from which to create compression. The other end of the stem can be attached to a spindle or housing of the compress assembly with a roughened surface that contacts the end of the bone. The stem can be engaged with a biasing element, such as a stack of curved washers, that can create compressive forces in the range of 1800 Newtons or more. This compressive force at the bone-implant interface can take advantage of Wolf's Law to stimulate formation of osseous integration of the bone with the implant.

While this construct has proven effective at creating a compressive interface and osseous integration in difficult clinical situations (especially in the setting of limited bone), there are a number of issues with some of these compress systems. For example, a compress construct does not resist bending loads very well. The anchor or stem can be designed to create a compressive force. Its outer diameter can be relatively small (just enough cross-sectional material to withstand the anticipated tension). This can create a situation where the recipient of a compress implant can be at a risk of fracture during the first several weeks postoperatively, until reactive bone forms and osseous integration of the spindle can be achieved. Early postoperative fractures have therefore been an issue with compress implants.

The success of many compress implants depends on their placement. Concentric placement of a device can be essential in its success. While the technique guide and instruments are excellent, a small amount of eccentricity can load the implant unevenly, which can lead to failure. Because (in part) of the design, some compress implants do not tolerate less than perfect placement.

Some patients who need fixation have poor biology. Compress implants rely less on mechanical fixation and more on biologic fixation over the long term. If the implant does not create osseous integration within a few weeks or months, it may not have enough stand-alone mechanical integrity to maintain fixation and will eventually fail mechanically.

Many patients who would be candidates for a compress implant have poor bone quality. Patients with multiple failed joint replacements, or cancers (requiring chemotherapy), or more recently the transdermal osseous integration candidates, all tend to have very poor bone quality. With an anchor plug that will be transmitting up to 3600 Newtons of compression through the cortical bone, poor bone quality may not be tolerated well in compress-type implants, which can lead to catastrophic failure if fracture occurs.

Intrinsic to some compress-type implants, is the creation of stress risers (or stress concentrations). A series of transverse pins can be placed through the bone and through the anchor plug to create a base for the compressive force to pull against. These transverse drill holes and pins can create a stress riser in this location, which, combined with poor bone quality, could result in a failure or fracture.

To utilize positive aspects of compress-type implants (long-term, biologically active osseous integration), while simultaneously addressing the issues discussed above, this disclosure proposes a hybrid compress stem as a solution. The hybrid compress can combine the benefits of traditional stem technology with the benefits of compress technology, satisfying the needs of patients and satisfying surgeons who may have concerns about the compress limitations. One solution can be to provide a press-fit or cemented stem, straight or curved, along with a compress mechanism at the bone implant interface. The press-fit or cemented stem can fill the role of traditional stems with strong early fixation, early stability in bending and torsion, and early intrinsic mechanical strength and fixation, while the compress mechanism can provide long-term osseous integration and can increase fixation.

Many clinicians like the idea of a compress, but are put off by its lack of immediate mechanical stability, difficulty of positioning, and implications of its use in those with poor bone quality or restricted biology. The hybrid design addresses those concerns and can provide clinicians a valuable tool in these difficult cases.

In one example, a spindle of a compress assembly can abut a bone face and can be contiguous with a distal stem section. The distal stem section can be a stem section of smooth, polished stem. The distal stem section can be slightly smaller in diameter than the endosteal diameter of the bone so as not to create a press or interference fit. The distal stem section can vary in length (depending on bone quality and clinical conditions). The distal stem section can avoid integration with bone, to allow the bone to compress longitudinally without resistance and to allow for compressive forces of the compress assembly to load the bone implant interface.

Under certain circumstances, a substance coating can be applied to the surface of the distal stem section to help reduce bone on-growth and/or to help prevent cement adhesion (should the clinician decide to cement a proximal portion of the stem for fixation). A proximal end of the distal stem section can include smooth cross-drilled receptacles or bores for to receive anchoring pins. The bores can be manufactured to reduce the stress riser effect within the stem.

The proximal stem section can continue from the distal stem section. The proximal stem section can be the portion of the hybrid stem that can help provide immediate fixation. The proximal stem section can help achieve immediate stability through press-fit or cemented means, depending on the clinical scenario and clinician preference. The proximal stem portion can also be of variable length. Short and long straight press fit stems can have either in-growth or on-growth surfaces, limited to the proximal stem portion, and can have endosteal flutes that can engage the endosteal cortex and can help to provide some immediate rotational stability.

The proximal stem section of can be press or interference fit to provide immediate fixation and stability of the implant. Longer curved press-fit stems may not require endosteal flutes, as they would be rotationally stable intrinsically in curved bone (i.e. femur). Short or long stems could also be cemented for immediate fixation, where a goal can be to limit the extent of the cement fixation to the proximal stem portion only. The entirety of the stem (proximal and distal stem portions) can be either straight or curved and of variable length. Longer stems will need to be curved to accommodate the anatomy in certain bones of the femur (i.e. femur).

Alternatively, the stem can be such that the distal stem portion can be entirely straight and such that the surface of the distal stem portion can be prepared in such a way that cement could not adhere to the surface of the distal stem portion, thereby allowing longitudinal compression through the distal stem portion to the compress assembly.

Figure 1:
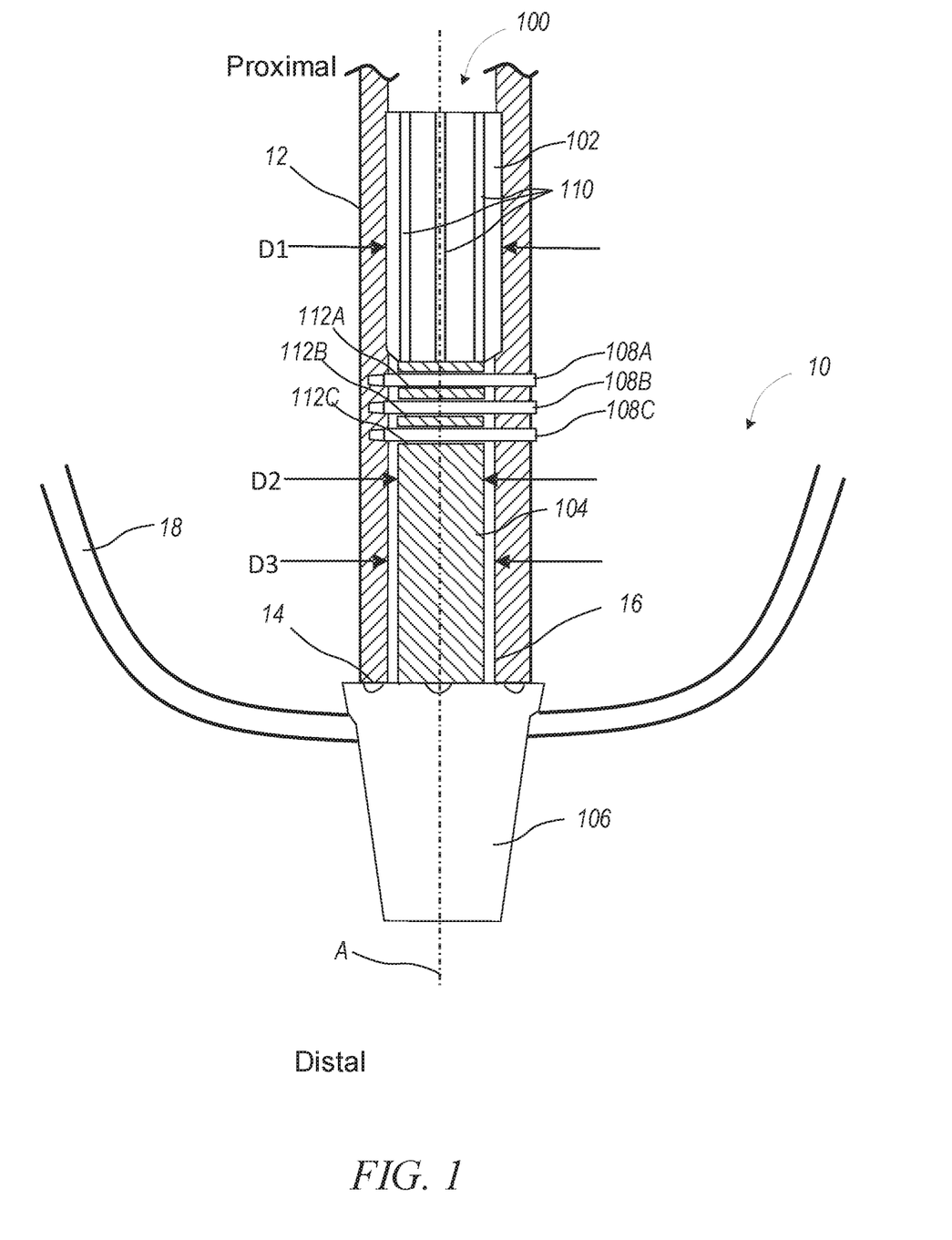
FIG. 1 illustrates a front cross-sectional view of an implant assembly and a leg, in accordance with at least one example of this disclosure.

FIG. 1 illustrates a front cross-sectional view of an implant assembly 100 and a leg 10, in accordance with at least one example of this disclosure. The implant assembly 100 can be a hybrid compress fixation system or assembly configured to secure a prosthesis to the leg 10.

The leg 10 can include a bone 12, including a resected distal portion 14, and an intramedullary canal 16. The leg 10 can also include a dermis portion 18. The implant assembly 100 can include a first stem portion 102, a second stem portion 104, a compress assembly 106, and pins 108A-108C. The first stem portion 102 can include flutes 110 and can have a diameter of D1. The second stem portion 104 can include bores 112A-112C and can have a diameter of D2. The intramedullary canal 16 of the bone 12 can have a diameter of D3. Also shown in FIG. 1 are orientation indicators Proximal and Distal and an axis A.

The leg 10 can be, in some examples, a superior or proximal leg portion, where the bone 12 is a femur, and the resected distal portion 14 is created during a procedure, such as an amputation and/or a femoral implant procedure, where the bone 12 of the femur is resected to create a surface to receive the compress assembly 106 thereon.

The first stem portion 102 can be a rigid or semi-rigid and elongate body extending substantially along axis A and connecting to the second stem portion 104 at a distal end of the first stem portion 104. In some examples, the first stem portion 102 can be comprised of biocompatible materials such as such as stainless steels, cobalt-chromium, titanium variations, polyether ether ketone (PEEK), and combinations thereof.

In some examples, the first stem portion 102 can have a substantially cylindrical shape (having a substantially consistent diameter D1). In other examples, the first stem portion can have other geometric shapes. For examples, the first stem portion 102 can be tapered from a proximal end of the first stem portion 102 to a distal end to make insertion into the intramedullary canal 16 easier and to help ensure an outer surface of the first stem portion engages an endosteum and/or compact bone of the bone 12.

Accordingly, the first stem portion 102 can have a diameter of D1 that is larger than the diameter D3 of the intramedullary canal, such that the first stem portion 102 can engage the bone 12 in a press-fit configuration or an interference fit arrangement between the first stem portion 102 and the bone 12 within the intramedullary canal 16.

In some examples, the first stem portion 102 can include flutes 110, which can be radial projections extending axially along an outer surface of first stem portion 102. The flutes 110 can be circumferentially disposed around first stem portion 102 and can be of a quantity of flutes 110 such as 1, 2, 3, 4, 5, 6, 10, 15, and the like. The flutes 110 can be configured to engage the endosteum and/or compact bone of the bone 12 to help prevent axial and rotational movement of the first stem portion 102 relative to the intramedullary canal 16 and the bone 12. The flutes 110 can thereby improve early fixation of the implant assembly 100 to the bone 12 before osseointegration occurs, which can help limit movement of the implant assembly 100 and can help prevent fractures of the bone 12 and the implant assembly 100.

In some examples, the flutes 110 can have a diameter that is larger than the diameter D3 of the intramedullary canal 16 to ensure an interference fit between the bone 12 and the flutes 110. In some of these examples, the diameter of the flutes 110 can be larger than the diameter D1 of the first portion 102, which can also be larger than the diameter D3 of the intramedullary canal 16, such that the first stem portion 102 can engage the bone 12 in an interference fit and the flutes 110 can extend radially further into the bone 12, to help further limit movement of the implant assembly 100, such as axial translation and rotation of the implant with respect to the bone 12.

In some examples, the first stem portion 102 can have a surface finish and/or can be made of a material configured to promote bone in-growth and/or on-growth, such as a porous surface finish, to enhance fixation (such as through osseointegration) of the first stem portion 102 to the bone 12. For example, one porous material the first stem portion 102 can be made of (or made partially of) is OsseoTi™ porous metal from Zimmer Biomet™ (Warsaw, Ind.). OsseoTi can be made out of Ti6A14V and can have a porous structure that generally mimics a porous structure of human cancellous bone. Also, the porous material can be Trabecular Metal™, also from Zimmer Biomet. Such a material can be formed from a reticulated vitreous carbon foam substrate that can be infiltrated and coated with a biocompatible metal, such as tantalum, such as using a chemical vapor deposition ("CVD") process in the manner disclosed in detail in U.S. Pat. No. 5,282,861. Also, the porous material can be Regenerex® can be used, also from Zimmer Biomet. In other examples, other porous materials can be used.

In some examples, the first stem portion 102 can be configured to be fixed to the bone 12 using a bone cement or adhesive. In these examples, the flutes 110 may or may not be included. In some examples, the first stem portion 102 can include ejection ports for ejecting adhesive therefrom through implant assembly 100.

The second stem portion 104 can be a rigid or semi-rigid and elongate body extending substantially along axis A and connecting to the first stem portion 102 at a distal end of the first stem portion 102 and a proximal end of the second stem portion 104. In some examples, the first stem portion 104 can be comprised of biocompatible materials such as such as stainless steels, cobalt-chromium, titanium variations, polyether ether ketone (PEEK), and combinations thereof.

The second stem portion 104 can have a diameter D2 that is smaller than the diameter D3 of the intramedullary canal 16 and, in some examples, smaller than the diameter D1 of the first stem portion 102. In some examples, the diameter D2 of the second stem portion 104 can be smaller than the diameter D3 of the intramedullary canal 16 such that contact between the second stem portion 104 and the intramedullary canal 16 is reduced to help limit friction or interaction between the second stem portion 104 and the bone 12 and to help reduce in-growth and on-growth onto the second stem portion 104. Further, the second portion 104 can have a smooth or polished surface to help reduce bone in-growth and on-growth. In other examples, one or more coatings or layers can be applied to the surface of the second stem portion 104 to help prevent in-growth and on-growth. By helping to reduce in-growth and on-growth, these features can help to allow the bone 12 to compress axially without resistance and can help to allow for compressive forces of the compress assembly to load the bone/implant interface.

Figure 2:
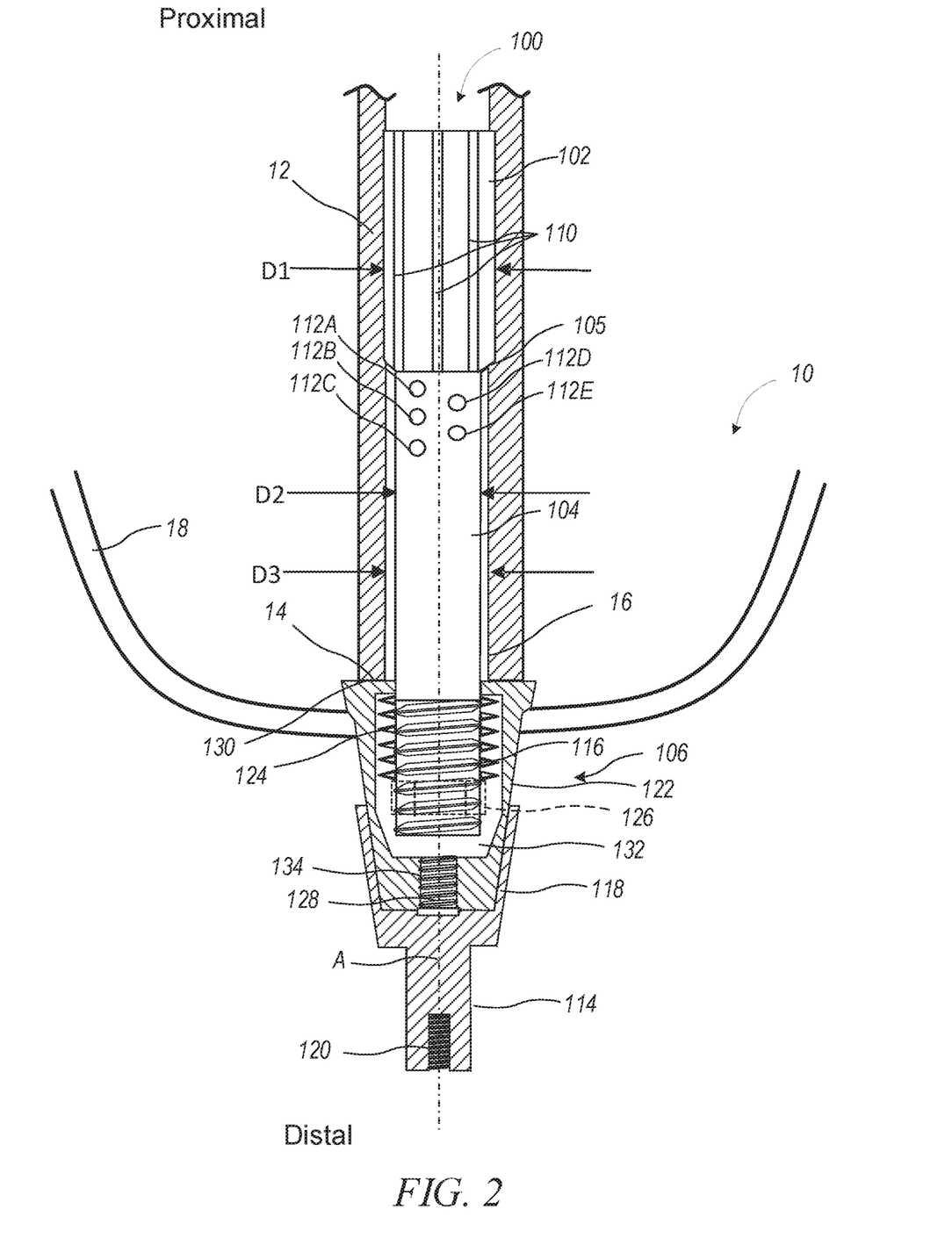
FIG. 2 illustrates a front cross-sectional of an implant assembly and a leg, in accordance with at least one example of this disclosure.

The second stem portion 104, can include bores 112A-112C, which can be bores extending through the second stem portion 104 substantially transversely to axis A. Though only three bores are shown in FIG. 1, the second stem portion 104 can include five bores, as shown in FIG. 2, and can include fewer or more bores in other examples, such as 1, 2, 3, 4, 6, 7, 8, 9, 10, or the like. In some examples, each of bores 112A-112C can be configured to receive one of the pins 108A-108C, respectively, therethrough.

In some examples, the pins 108A-108C can be rigid or semi-rigid and elongate fasteners configured to secure the bone 12 to the second stem portion 104. In some examples, each of the pins 108A-108C can have a tapered profile and/or a sharp or tapered tip. In some examples, each of the pins 108A-108C can be other types of fasteners, such as a screw, rivet, or the like.

Lengths of each of the first stem portion 102 and the second stem portion 104 can vary depending on bone quality and clinical conditions. In some examples, the lengths of one or more of the first stem portion 102 and the second stem portion 104 can be optimized for a patient. Similarly, curvature or both the first stem portion 102 and the second stem portion 104 can vary depending on clinical conditions, such as bone quality, and available length of the femur for implant insertion. In examples where a curved first stem portion 102 and/or second stem portion 104 is used, fluting may not be required.

The compress assembly 106 can be configured to couple to the second stem portion 104 at a distal portion of the second stem portion 104. The compress assembly 106 can also be configured to engage the distal resected portion 14 of the bone 12 to apply a compressive force to the bone 12. The components of the compress assembly 106 are discussed in further detail below with respect to FIG. 2.

In operation of some examples, the bone 12 can be resected to create the resected distal portion 14. Following resection and preparation, the first stem portion 102 can be inserted distally to proximally into the intramedullary canal 16 of the bone 12. In some examples, cement or adhesive can be applied to the first stem portion 102 before, during, and/or after insertion into the intramedullary canal 16. The first stem portion 102 of implant assembly 100 can be inserted into the bone 12 distally to proximally, such that the first stem portion 102 engages the endosteum of the bone 12 in an interference or press-fit arrangement. In some examples, the flutes 110 can also engage the endosteum of the bone 12. The first stem portion 102 can be inserted into the intramedullary canal 16 of the bone 12 until the second stem portion 104 is disposed within the bone 12 and until the compress assembly 106 contacts the distal resected portion 14 of the bone 12.

In some examples, pilot or guide holes can be drilled through the bone 12 to align with the bores 112A-112C. These holes can be pre-drilled into bone 12 using guide tools, in some examples. The bores 112A-112C can be aligned with respective holes through the bone 12 so that pins 108A-108C can be passed through respective bores 112A-112C, as shown in FIG. 1. Pins 108A-108C can thereby secure the second stem portion 104 to the bone 12. The engagement of the first stem portion 102 with the endosteum (and in some cases compact bone) of the bone 12 can help provide near immediate transmission of forces between the bone 12 and an external prosthesis, which can help reduce a possibility of fracture prior to osseointegration of the implant assembly 100. In some examples, engagement of the flutes 110 with the endosteum of the bone 12 and/or adherence of the first stem portion 102 to the bone 12 using an adhesive can further help provide near immediate transmission of forces between the bone 12 and an external prosthesis. In this way, the features of implant assembly 100 can provide a balance of long-term mechanical integrity through osseous integration from the second stem portion 104 and the compress assembly 106 with early fixation provided by a mechanical stem (the first stem portion 102).

FIG. 2 illustrates a front cross-sectional view of the implant assembly 100 and the leg 10, in accordance with at least one example of this disclosure. The implant assembly 100 shown in FIG. 2 can be the same as the implant assembly 100 of FIG. 1; however, FIG. 2 shows additional details of the implant assembly 100.

The implant assembly 100 can include the first stem portion 102, the second stem portion 104, the compress assembly 106, and a prosthesis adapter 114. The first stem portion 102 can include flutes 110 and can have the diameter of D1. The second stem portion 104 can include bores 112A-112E, a threaded portion 116, and can have the diameter of D2. The prosthesis adapter 114 can include a tapered bore 118, and a threaded female bore 120. The compress assembly 106 can include a housing 122, a biasing element 124, a stem retainer 126, and a plug 128. The housing 122 can include a proximal housing portion 130, a cavity 132, and a plug bore 134. The intramedullary canal 16 of the bone 12 can have the diameter of D3. Also shown in FIG. 2 are orientation indicators Proximal and Distal and an axis A.

Because the first stem portion 102 can have a greater diameter than the second stem portion 104, the second stem portion 104 can be connected to the first stem portion 102 at a transition 105. In some examples, the transition 105 can be a round, chamfer, bevel, J groove, combination thereof, or the like. The transition 105 can help prevent a stress concentration or stress riser between the first stem portion 102 and the second stem portion 104.

The second stem portion 104 can include bores 112A-112E in a staggered pattern to accommodate multiple fasteners therethrough, as discussed in detail in FIG. 1 above. In other examples, other patterns can be used and other quantities of bores can be used. In some examples, the bores 112A-112E can include edges that include a round, chamfer, bevel, J groove, combination thereof, or the like, to help reduce a stress concentration or stress riser at each of the bores 112A-112E.

The second stem portion 104 can extend axially distally at a substantially consistent diameter, D2, throughout a length of the second stem portion 104, such as from the transition 105 through the threaded portion 116. As discussed further below, the diameter D2 of the second stem portion 104 can be large enough to transfer loads between the first stem portion and the compress assembly (and therefore an external prosthesis) to help avoid stem or bone fracture prior to osseointegration of the implant and the bone. In other examples, the diameter of the second stem portion 104 can vary along the length of the second stem portion 104.

In some examples, stem retainer 126 can be a nut; however, in other examples, stem retainer 126 can be other types of fasteners. In one example, the biasing element 124 can be a washer stack sized and configured to receive threaded portion 116 of the second stem portion 104 therethrough. In some examples, biasing element 124 can be other types of resilient elements, such as a coil spring, one or more wave springs, or the like. In other examples, biasing element 124 can be one or more compressible and resilient members comprised of resilient materials such as rubbers, plastic, and the like.

The threaded portion 116 of the second stem portion 104 can be located at a distal portion of the second stem portion 104 and can be insertable into the cavity 132 of the housing 122 and through biasing element 124 and can be secured therein by the stem retainer 126. The stem retainer 126 can also engage a distal portion of the biasing element 124, compressing the biasing element between the housing 122 and the stem retainer 126, simultaneously securing the threaded portion 116 within the housing 122 and securing the biasing element 124 between the housing 122 and the stem retainer 126. In some examples, the stem retainer 126 can be threaded onto the threaded portion 116 to compress the biasing element to achieve a desired force applied to the housing 122 and the stem retainer 126 (and therefore to the second portion of the stem 104).

The prosthesis adapter 114 can include a tapered bore 118 configured to engage an outer taper of housing 122 such that the prosthesis adapter 114 and the housing 122 engage in a taper-to-taper arrangement. In some examples, the tapered bore 118 and the housing 122 can have one consistent taper and in other examples, the tapered bore 118 and the housing 122 can have multiple tapered portions of varying taper sizes and/or styles including Brown, Morse, Jarno, Jacobs, and the like tapers. The threaded female bore 120 of the prosthesis adapter can be configured to receive a fastener (such as a screw or bolt) secure an external prosthesis to the prosthesis adapter.

The plug 128 can be a member insertable into and securable within the plug bore 134 of the housing 122 to seal the cavity 132 of the housing 122. In some examples, the plug 128 can be a threaded member, threadably securable to the plug bore 134 of the housing 122. The proximal housing portion 130 can be a proximal portion of the housing 122 and can be comprised of materials configured to support bone ingrowth and/or ongrowth to enhance fixation of the housing 122 to the bone 12 (such as through osseointegration), such as Trabecular Metal™, Regenerex®, or OsseoTi®, described above, a roughened surface, and/or hydroxyapatite.

In operation, after the first stem portion 102 and the second stem portion 104 have been inserted into and secured to the bone 102, the biasing element 124 can be secured around the second stem portion 104 using the stem retainer 126. The biasing element 124 can be compressed and retained within the housing 122 before or during the procedure. The stem retainer 126 can be threadably secured to the second stem portion 104 such that biasing element 124 applies a substantially distally directed force on stem retainer 126, which is transferred to second stem portion 104 and to pins 108A-108E and ultimately to bone 12. The biasing element 124 also applies a substantially proximally directed force on housing 122 which is transferred to the distal resected portion 14 of bone 12. In other words, the biasing element 124 is configured to bias the housing 122 proximally and to bias the second stem portion 104 distally. These forces combine to impose a pair of forces that compress the distal portion of bone 12 (between pins 108A-108E and the distal resected portion 14 of bone 12). The compression can stimulate an increase in bone density and osseointegration of the implant assembly 100 with bone 12.

Because the diameter D2 of the second stem portion 104 is not much smaller than the intramedullary canal 16, the second stem portion is strong enough to transfer loads between the first stem portion and the compress assembly (and therefore an external prosthesis) to help avoid stem or bone fracture prior to osseointegration of the implant and the bone. For example, the second stem portion 104 can transmit non-axial compressive loads, such as eccentric loads and can accordingly transfer bending moments. This can help prevent fracture or breakage of the implant assembly 100 and can help reduce fracture of the bone 12.

Figure 3:
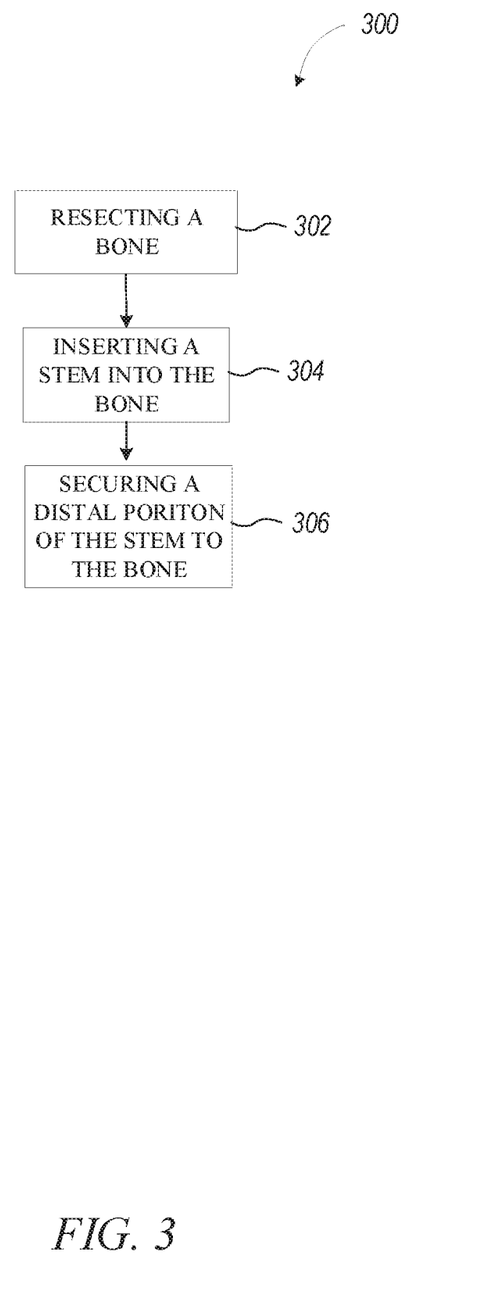
FIG. 3 illustrates a schematic view of a method, in accordance with at least one example of this disclosure.

FIG. 3 illustrates a schematic view of method 300, in accordance with at least one example of this disclosure. Method 300 can be a method of securing an implant to a bone. The steps or operations of method 300 are illustrated in a particular order for convenience and clarity; many of the discussed operations can be performed in a different sequence or in parallel without materially impacting other operations. Method 300, as discussed, includes operations performed by multiple different actors, devices, and/or systems. It is understood that subsets of the operations discussed in method 300 attributable to a single actor, device, or system could be considered a separate standalone process or method.

Method 300 can begin at step 302 where a bone can be resected. For example, the bone 12 of FIGS. 1 and 2 can be resected to create the distal resected portion 14. In step 304, a stem can be inserted into the bone. For example, the first stem portion 102 of implant assembly 100 can be inserted into the bone 12 distally to proximally, such that the first stem portion 102 engages the bone 12 in an interference or press-fit arrangement. The first stem portion 102 can be inserted until the second stem portion 104 is disposed within the bone 12 and until the compress assembly 106 contacts the distal resected portion 14 of the bone 12.

At step 306, the second stem portion can be secured to the bone. For example, the second stem portion 104 can be secured to the bone 12. In some examples, pilot or guide holes can be drilled through the bone to align with bores of the second stem portion (typically prior to stem insertion into the bone). For example, holes can be drilled through the bone 12 such that the bores 112A-112C align with respective holes through the bone 12 following insertion of the first stem portion 102 and the second stem portion 104 into the bone. Once the bores of the bone 12 are aligned with the bores 112A-112C, fasteners, such as pins 108A-108C, can be secured to the bone 12 and to the second stem portion 104 by passing through respective bores 112A-112C.

Thereafter, the biasing element 124 can be compressed and retained within the housing 122 using stem retainer 126 to secure the housing 122 to the second stem portion 104 at the threaded portion 116.

NOTES AND EXAMPLES

The following, non-limiting examples, detail certain aspects of the present subject matter to solve the challenges and provide the benefits discussed herein, among others.

Example 1 is a stem for fixating a prosthesis to a bone, the stem comprising: a first stem portion extending substantially along a longitudinal axis, the first stem portion including a first diameter larger than a diameter of an intramedullary canal of a bone such that the first stem portion is configured to engage the bone, the first stem portion including a distal portion; and a second stem portion extending substantially distally from the distal portion of the first stem portion along the longitudinal axis, the second stem portion including a second diameter smaller than the first diameter and smaller than the diameter of the intramedullary canal of the bone, the second stem portion securable to the bone independent of the first stem portion, and the second stem portion including a distal portion couplable to a compress assembly.

In Example 2, the subject matter of Example 1 optionally includes wherein the first diameter is sized such that the first stem portion engages the bone in an interference-fit.

In Example 3, the subject matter of any one or more of Examples 1-2 optionally include wherein the second stem portion includes a plurality of bores each configured to receive a fastener therethrough to secure the second stem portion to the bone independent of the first stem portion.

In Example 4, the subject matter of any one or more of Examples 1-3 optionally include wherein the first portion includes a plurality of flutes extending radially from a surface of the first stem portion, extending substantially axially along the first stem portion, and spaced around a circumference of the first portion, each of the plurality of flutes configured to engage the bone to limit rotation of the stem relative to the bone.

In Example 5, the subject matter of any one or more of Examples 1-4 optionally include wherein the second stem portion includes a polished outer surface to limit bone on-growth.

In Example 6, the subject matter of any one or more of Examples 1-5 optionally include wherein the first stem portion and the second stem portion are connected by one of a fillet, chamfer, bevel, or round.

In Example 7, the subject matter of any one or more of Examples 1-6 optionally include wherein the first stem portion includes an outer surface comprised of a porous material configured to promote bone ingrowth.

In Example 8, the subject matter of Example 7 optionally includes V and has a porous structure that substantially mimics a porous structure of human cancellous bone.

In Example 9, the subject matter of any one or more of Examples 1-8 optionally include wherein the distal portion of the second stem portion includes a threaded portion configured to receive a fastener to secure the second stem portion to a biasing element.

In Example 10, the subject matter of any one or more of Examples 1-9 optionally include wherein the diameter of the second stem portions is substantially consistent along an axial length of the second stem portion between a distal end of the second stem portion and a transition between the first portion and the second portion.

Example 11 is a hybrid compress fixation system for securing a prosthesis to a bone, the system comprising: a compress assembly including a proximal portion engageable with a resected distal portion of a bone and distal portion securable to a prosthesis; a stem comprising: a first stem portion extending substantially along a longitudinal axis, the first stem portion including a first diameter larger than a diameter of an intramedullary canal of a bone such that the first stem portion is configured to engage the bone, the first stem portion including a distal portion; and a second stem portion extending substantially distally from the distal portion of the first stem portion along the longitudinal axis, the second stem portion including a second diameter smaller than the first diameter and smaller than the diameter of the intramedullary canal of the bone, the second stem portion securable to the bone independent of the first stem portion, and the second stem portion including a distal portion couplable to the compress assembly.

In Example 12, the subject matter of Example 11 optionally includes wherein the compress assembly includes a housing configured to receive the second stem portion therein, the housing including a proximal portion engageable with the resected distal portion of the bone.

In Example 13, the subject matter of Example 12 optionally includes wherein the compress assembly includes a biasing element disposable within the housing and configured to engage the second stem portion and the housing to bias the housing proximally and to bias the second stem portion distally.

In Example 14, the subject matter of Example 13 optionally includes wherein the compress assembly includes a fastener securable to the distal portion of the second portion to engage and retain the biasing element.

In Example 15, the subject matter of any one or more of Examples 12-14 optionally include wherein the compress assembly includes a taper adapter including a proximal tapered bore configured to engage a distal taper of the housing to secure the taper adapter to the housing in a taper-to-taper configuration.

In Example 16, the subject matter of Example 15 optionally includes wherein the distal adapter is securable to the prosthesis.

Example 17 is a stem for fixating a prosthesis to a bone, the stem comprising: a first stem portion extending substantially along a longitudinal axis, the first stem portion including a first diameter larger than a diameter of an intramedullary canal of a bone such that the first stem portion is configured to engage the bone, the first stem portion including a distal portion; and a second stem portion extending substantially distally from the distal portion of the first stem portion along the longitudinal axis, the second stem portion including a diameter that is substantially consistent along an axial length of the second stem portion between a distal end of the second portion and a connection between the first portion and the second portion, and the second stem portion including a distal portion couplable to a compress assembly.

In Example 18, the subject matter of Example 17 optionally includes wherein the second stem portion is securable to the bone independent of the first stem portion, and wherein the second diameter is smaller than the first diameter and smaller than the diameter of the intramedullary canal of the bone.

In Example 19, the subject matter of any one or more of Examples 17-18 optionally include wherein the first portion includes a plurality of flutes extending substantially axially and spaced around a circumference of the first portion, each of the plurality of flutes configured to engage the intramedullary canal to limit rotation of the stem relative to the bone.

In Example 20, the subject matter of any one or more of Examples 17-19 optionally include wherein the first diameter is sized such that the first stem portion engages the bone in an interference-fit.

In Example 21, the subject matter of any one or more of Examples 17-20 optionally include wherein the second stem portion includes a plurality of bores each configured to receive a fastener therethrough to secure the second portion to the bone.

In Example 22, the subject matter of any one or more of Examples 17-21 optionally include wherein the second stem portion includes a polished outer surface to limit bone on-growth.

In Example 23, the apparatuses or method of any one or any combination of Examples 1-22 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A stem for fixating a prosthesis to a bone, the stem comprising:
a first stem portion extending along a longitudinal axis, the first stem portion including a first diameter configured to be larger than a diameter of an intramedullary canal of the bone such that the first stem portion is configured to engage the bone in an interference fit between the first stem portion and the bone to secure the first stem portion to the bone, the first stem portion including a distal portion, the first stem portion including an outer surface comprising a porous material configured to promote bone ingrowth, the first portion including a plurality of projections extending radially from the outer surface of the first stem portion, the plurality of projections extending axially along the first stem portion, and the plurality of projections spaced around a circumference of the first portion, each of the plurality of projections configured to engage the bone to limit rotation of the stem relative to the bone; and
a second stem portion extending distally from the distal portion of the first stem portion along the longitudinal axis, the second stem portion including a second diameter smaller than the first diameter and configured to be smaller than the diameter of the intramedullary canal of the bone, the second stem portion securable to the bone, and the second stem portion including a distal portion couplable to a compress assembly, the second stem portion comprising:
a polished outer surface to limit bone on-growth; and
a plurality of bores each configured to receive a fastener therethrough to secure the second stem portion to the bone in addition to the interference fit between the first stem portion and the bone.

2. The stem of claim 1, wherein the first stem portion and the second stem portion are connected by one of a fillet, chamfer, bevel, or round.

3. The stem of claim 1, wherein the outer surface of the first stem portion is made of Ti6A14V and has a porous structure that is configured to mimic a porous structure of human cancellous bone.

4. The stem of claim 1, wherein the distal portion of the second stern portion includes a threaded portion configured to receive a fastener to secure the second stem portion to a biasing element.

5. The stern of claim 1, wherein the diameter of the second stem portion is consistent along an axial length of the second stem portion between a distal end of the second stem portion and a transition between the first portion and the second portion.

6. A hybrid compress fixation system for securing a prosthesis to a bone, the system comprising:

a compress assembly including a proximal portion engageable with a resected distal portion of the bone and distal portion securable to the prosthesis; and a stem comprising:

a first stem portion extending along a longitudinal axis, the first stem portion including a first diameter configured to be larger than a diameter of an intramedullary canal of the bone such that the first stem portion is configured to engage the bone in an interference fit between the first stem portion and the bone to secure the first stem portion to the bone, the first stem portion including a distal portion, the first stem portion including an outer surface comprising a porous material configured to promote bone ingrowth, the first portion including a plurality of projections extending radially from the outer surface of the first stem portion, the plurality of projections extending axially along the first stem portion, and the plurality of projections spaced around a circumference of the first portion, each of the plurality of projections configured to engage the bone to limit rotation of the stem relative to the bone; and a second stem portion extending distally from the distal portion of the first stem portion along the longitudinal axis, the second stem portion including a second diameter smaller than the first diameter and configured to be smaller than the diameter of the intramedullary canal of the bone, the second stem portion securable to the bone, and the second stem portion including a distal portion couplable to the compress assembly, the second stem portion comprising:

a plurality of bores each configured to receive a fastener therethrough to secure the second stem portion to the bone in addition to the interference fit between the first stem portion and the bone.

7. The stem of claim 6, wherein the compress assembly includes a housing configured to receive the second stem portion therein, the housing including a proximal portion engageable with the resected distal portion of the bone.

8. The stem of claim 7, wherein the compress assembly includes a biasing element disposable within the housing and configured to engage the second stem portion and the housing to bias the housing proximally and to bias the second stem portion distally.

9. The stem of claim 8, wherein the compress assembly includes a fastener securable to the distal portion of the second portion to engage and retain the biasing element.

10. The stem of claim 7, wherein the compress assembly includes a taper adapter including a proximal tapered bore configured to engage a distal taper of the housing to secure the taper adapter to the housing in a taper-to-taper configuration.

11. The stem of claim 10, wherein the taper adapter is securable to the prosthesis.

12. A stem for fixating a prosthesis to a bone, the stem comprising:

a first stem portion extending along a longitudinal axis, the first stem portion including a first diameter configured to be larger than a diameter of an intramedullary canal of the bone such that the first stem portion is configured to engage the bone in an interference fit between the first stem portion and the bone, the first stem portion including a distal portion, the first stem portion including an outer surface comprising a porous material configured to promote bone ingrowth, the first portion including a plurality of projections extending radially from the outer surface of the first stem portion, the plurality of projections extending axially along the first stem portion, and the plurality of projections spaced around a circumference of the first portion, each of the plurality of projections configured to engage the bone to limit rotation of the stem relative to the bone; and a second stem portion extending distally from the distal portion of the first stem portion along the longitudinal axis, the second stem portion including a diameter that is consistent along an axial length of the second stem portion between a distal end of the second portion and a connection between the first portion and the second portion, and the second stem portion including a distal portion couplable to a compress assembly, the second stem portion comprising:

a plurality of bores each configured to receive a fastener therethrough to secure the second stem portion to the bone in addition to the interference fit between the first stem portion and the bone.

13. The stem of claim 12, wherein the second stem portion is securable to the bone, and wherein the second diameter is smaller than the first diameter and configured to be smaller than the diameter of the intramedullary canal of the bone.

* * * * *

UNITED STATES PATENT AND TRADEMARK OFFICE
CERTIFICATE OF CORRECTION

Page 1 of 1

PATENT NO. : 10,857,009 B2
APPLICATION NO. : 16/017184
DATED : December 8, 2020
INVENTOR(S) : Ronald Raymond Hugate, Jr.

It is certified that error appears in the above-identified patent and that said Letters Patent is hereby corrected as shown below:

On the Title Page

In item (57), in "Abstract", in Column 2, Line 2, delete "stern" and insert --stem-- therefor In the Claims In Column 12, Line 58, in Claim 4, delete "stern" and insert --stem-- therefor In Column 12, Line 61, in Claim 5, delete "stern" and insert --stem-- therefor In Column 13, Line 12, in Claim 6, delete "stern" and insert --stem-- therefor In Column 13, Line 20, in Claim 6, delete "stern" and insert --stem-- therefor In Column 13, Line 26, in Claim 6, delete "stern" and insert --stem-- therefor In Column 14, Line 10, in Claim 12, delete "stern" and insert --stem-- therefor In Column 14, Line 13, in Claim 12, delete "stern" and insert --stem-- therefor In Column 14, Line 34, in Claim 12, delete "stern" and insert --stem-- therefor Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*